United States Patent [19]

Esler

[11] Patent Number: 5,792,183

[45] Date of Patent: Aug. 11, 1998

[54] COMBINATION PACEMAKER AND DEFIBRILLATOR HAVING DYNAMIC VENTRICULAR REFRACTORY PERIOD

[75] Inventor: James A. Esler, Columbia Heights, Minn.

[73] Assignee: Cardiac Pacemakers, Inc., St. Paul, Minn.

[21] Appl. No.: 790,763

[22] Filed: Jan. 27, 1997

[51] Int. Cl.$^6$ .................................................. A61N 1/00
[52] U.S. Cl. ........................................................ 607/4
[58] Field of Search .......................... 607/4, 5, 6, 14, 607/9

[56] References Cited

U.S. PATENT DOCUMENTS

| | | |
|---|---|---|
| 4,945,909 | 8/1990 | Fearnot et al. .................... 607/14 |
| 5,105,810 | 4/1992 | Collins et al. . |
| 5,111,816 | 5/1992 | Pless et al. . |
| 5,129,393 | 7/1992 | Brumwell . |
| 5,144,947 | 9/1992 | Wilson . |
| 5,179,947 | 1/1993 | Meyerson et al. . |
| 5,301,669 | 4/1994 | Duncan . |
| 5,334,222 | 8/1994 | Salo et al. . |

Primary Examiner—Scott M. Getzow
Attorney, Agent, or Firm—Haugen and Nikolai, P.A.

[57] ABSTRACT

An implantable cardiac stimulator having a bradycardia pacer and a defibrillator in a common housing and sharing common atrial and ventricular sense circuits includes circuitry for defining a dynamic paced refractory interval that is inversely proportional to the pacing rate to thereby allow adequate time in the cardiac cycle for sensing ventricular events even at elevated pacing rates such as when the atrial tracking rate approaches a programmed upper rate limit for the pacemaker or a sensor driven rate approaches the programmed upper rate limit.

3 Claims, 6 Drawing Sheets

| INDEX | RATE | | VR (ms) |
|---|---|---|---|
| | HIGH (b/m) | LOW (b/m) | |
| 0 | | 975.24 | 150 |
| 1 | 975.24 — | 483.78 | 150 |
| 2 | 483.78 — | 321.68 | 150 |
| 3 | 321.68 — | 240.94 | 150 |
| 4 | 240.94 — | 192.60 | 150 |
| 5 | 192.60 — | 160.42 | 150 |
| 6 | 160.42 — | 137.45 | 150 |
| 7 | 137.45 — | 120.23 | 150 |
| 8 | 120.23 — | 106.85 | 150 |
| 9 | 106.85 — | 95.15 | 175 |
| 10 | 95.15 — | 87.40 | 187 |
| 11 | 87.40 — | 80.10 | 200 |
| 12 | 80.10 — | 73.94 | 212 |
| 13 | 73.93 — | 68.65 | 225 |
| 14 | 68.65 — | 64.07 | 237 |
| 15 | 64.07 — | 60.06 | 250 |
| 16 | 60.05 — | 56.52 | 250 |
| 17 | 56.52 — | 53.38 | 250 |

FIG. 5

COMBINATION PACEMAKER AND DEFIBRILLATOR HAVING DYNAMIC VENTRICULAR REFRACTORY PERIOD

BACKGROUND OF THE INVENTION

I. Field of the Invention

This invention relates generally to cardiac rhythm management apparatus, and more particularly to an implantable pacemaker and defibrillator incorporating a dynamic ventricular refractory period following each paced beat wherein the length of the refractory period is inversely proportional to the rate at which a pacemaker is generating ventricular stimulating pulses.

II. Discussion of the Prior Art

Implantable cardiac rhythm management devices have been devised in which both a pacemaker and a programmable defibrillator are combined in a common housing and, thus, may be used in the treatment of bradycardia and tachycardiac, as well as for ventricular fibrillation. For example, the Pless et al. U.S. Pat. No. 5,111,816 issued to Ventritex Corporation describes a combined pacemaker/defibrillator that shares a common sensing amplifier network for receiving and processing atrial and ventricular depolarization signals which are then delivered to a microprocessor-type controller for determining various timing intervals between the depolarization signals for determining whether bradycardia pacing is an appropriate therapy or whether antitachy pacing and/or defibrillation is required.

If the pacemaker circuitry is programmed to operate in an atrial tracking mode, or if the pacemaker is designed to be rate responsive, it is common for the pacemaker to have a programmable lower rate limit (LRL) and a programmable upper rate limit (URL) and where the ventricular rate tracks the atrial rate between these two limits or, in the case of a rate adaptive pacemaker, where the pacing rate varies between the two limits depending upon the patient's activity or hemodynamic state being sensed.

It is also common in pacemaker design to include a paced refractory period following the occurrence of a ventricular pacing pulse during which time the ventricular sense amplifier is inhibited so that depolarization events occurring during the ventricular refractory period are ignored. The paced refractory period of the prior art pacemakers is typically a fixed value, programmed by the physician of a length sufficient to insure that T-wave are not sensed at or near the LRL. When operating at or near the LRL, an adequate sensing window exists between the termination of the paced ventricular refractory period and the occurrence of the next paced ventricular beat in which ventricular depolarization events can be sensed. However, when the atrial rate increases or the physiologic sensor dictates a ventricular rate approaching the URL, the ventricular sensing window becomes very short relative to the V—V interval, thus degrading the ability of the defibrillator to quickly detect ventricular arrhythmias. One way to obviate this problem would be to include in the combined pacemaker and defibrillator, separate atrial and ventricular sensing circuits for each device, but there is a price associated with that approach in terms of battery life. It is much more advantageous that only a single atrial and ventricular sense circuit be shared by the pacer and by the defibrillator.

SUMMARY OF THE INVENTION

The present invention provides a combined pacemaker and defibrillator that share common atrial and ventricular sensing circuitry but which utilizes a dynamic paced ventricular refractory period whose length is inversely proportional to the ventricular pacing rate. As the ventricular pacing rate increases, the paced refractory period becomes shorter, thereby still allowing an adequate sensing window whereby the microprocessor controlling the defibrillator receives sufficient information for detecting episodes of tachycardia or fibrillation so that appropriate therapy can be delivered for terminating same.

In accordance with the present invention, there is provided an implantable cardiac stimulator comprising a first means for sensing atrial depolarization events, a second means for sensing ventricular depolarization events and a third means for generating ventricular stimulating pulses. The first and second means provide information to a microprocessor-based controller device used to control the time at which the ventricular stimulating pulses are generated. The microprocessor-based controller device establishes a dynamic refractory period that is initiated in substantial time coincidence with the generation of each ventricular stimulating pulse and which ends at a time dependent upon the rate at which the ventricular stimulating pulses are being generated. In particular, the length of the paced ventricular refractory period is made inversely proportional to the rate at which the ventricular stimulating pulses are being generated. Thus, at elevated pacing rates approaching the URL, the paced ventricular refractory period is sufficiently short to still provide an adequate sensing window for detecting tachyarrhythmias and/or ventricular fibrillation, allowing the defibrillator circuitry to initiate a preprogrammed therapy designed to terminate the arrhythmia.

DESCRIPTION OF THE DRAWINGS

FIG. 5 is a table stored in the memory of the microprocessor of FIG. 2 in which preprogrammed values for paced ventricular refractory intervals are stored.

DESCRIPTION OF THE PREFERRED EMBODIMENT

Figure 1:
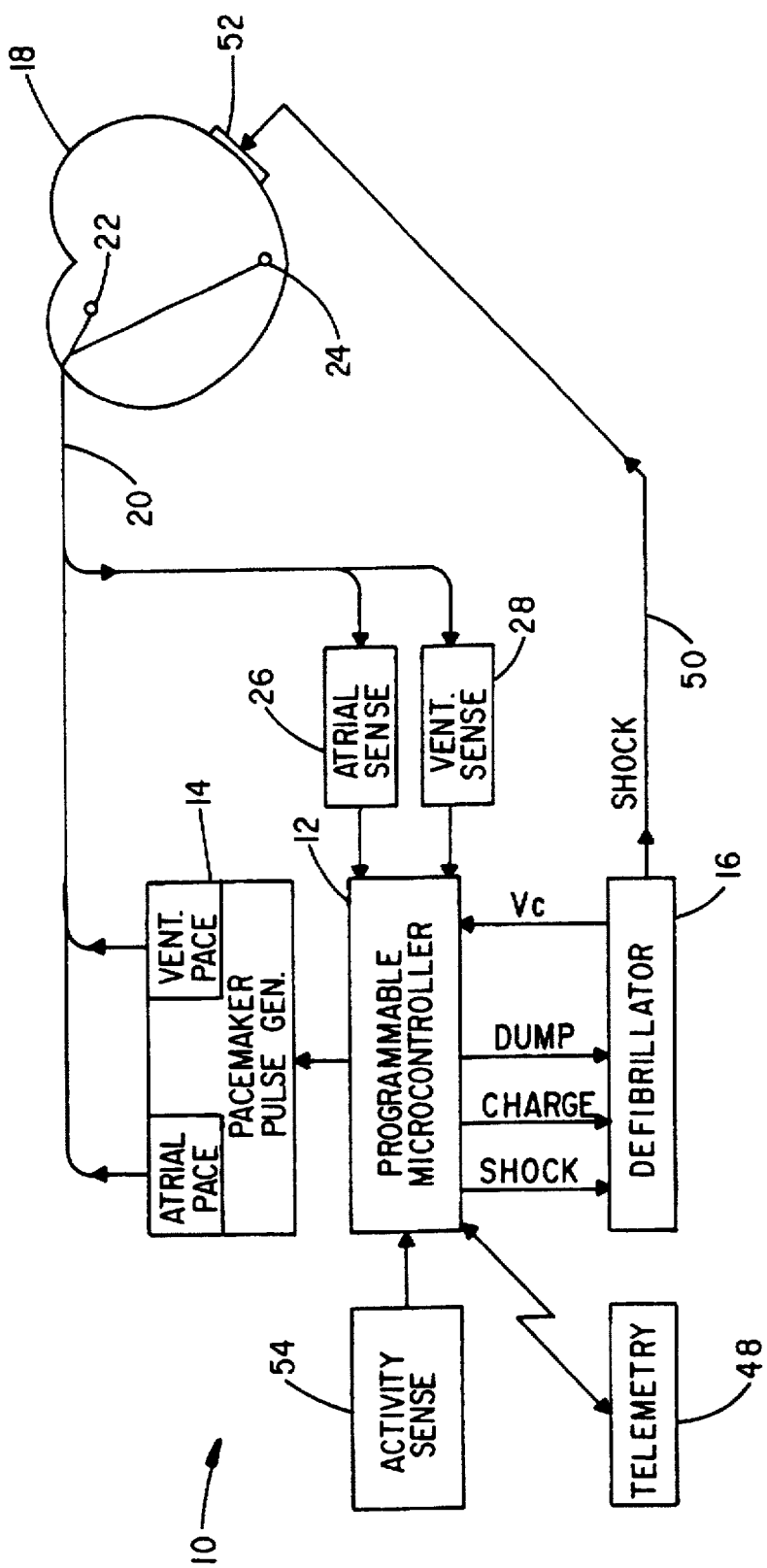
FIG. 1 is a block diagram of a combined pacemaker/defibrillator in which the present invention finds use.

Referring to FIG. 1, there is illustrated a block diagram of an implantable cardiac rhythm management device embodying the present invention. It is indicated generally by numeral 10 and the intelligence for controlling the system is resident in a programmable microcontroller 12 which oversees the operation of both a bradycardia pacemaker 14 and a defibrillator 16.

The pacemaker portion of the system, identified by numeral 14, is connected to a heart 18 by means of an endocardial lead 20 having first electrodes 22 for sensing atrial activity and second electrodes 24 for sensing and pacing one or both ventricles. The atrial sensing electrode 22 is coupled by a conductor in the lead 20 to an atrial sense amplifier/filter circuit 26 whose output is fed to the programmable microcontroller 12. Likewise, the ventricular sense electrode 24 is coupled through a conductor in the lead 20 to a ventricular sense amplifier/filter 28 and its output is also fed to the programmable microcontroller 12. It is to be noted that even though the implantable rhythm management device 10 incorporates both a bradycardia pacemaker pulse generator 14 and a defibrillator 16, only a single atrial sense circuit 26 and a single ventricular sense circuit 28 is utilized therein.

Those skilled in the art can appreciate that if a unipolar lead arrangement is employed, only a single electrode 24 need be incorporated on the lead 20 in that the metal can of the pacemaker/defibrillator housing may serve as the indifferent electrode. In the case of a bipolar lead arrangement, two relatively closely spaced electrodes are positioned within the right ventricular chamber of the heart.

Figure 2:
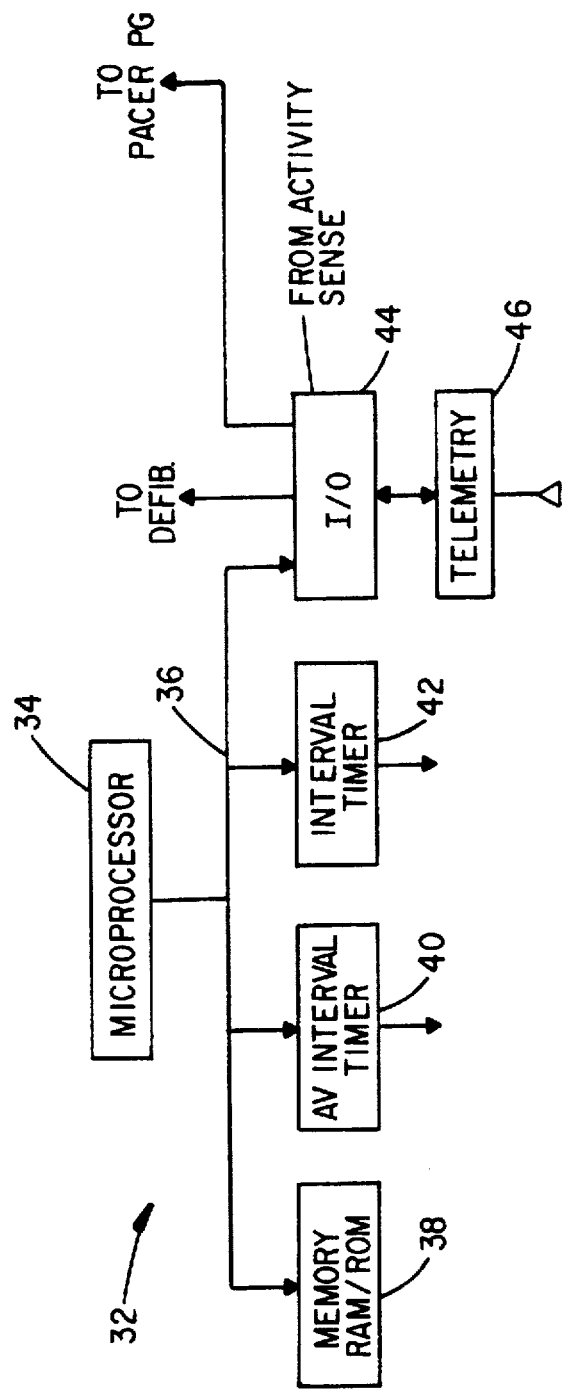
FIG. 2 is a block diagram of the programmable microcontroller of FIG. 1.

The programmable microcontroller 12 is identified generally by numeral 32 in FIG. 2 and comprises a microprocessor 34 having an internal bus 36 allowing bidirectional communication with a memory 38, and an A-V interval timer 40, a V—V interval timer 42 and an input/output circuit 44. A telemetry circuit 46 may be coupled to an I/O port of circuit 44 to permit two-way communication between the implanted cardiac rhythm management device 10 and an external telemetry programmer 48.

In addition to controlling the pacemaker pulse generator 14, the programmable microcontroller 12 also is connected in controlling relation to an implantable defibrillator circuit 16 capable of providing a high energy shock over lead 50 to an appropriate electrode 52, here shown as an epicardial patch. In particular, the programmable microcontroller 12 may be responsive to the frequency and rate of onset of ventricular depolarization signals picked up by the ventricular sense amplifier/filter 28 and, in accordance with a prescribed algorithm, a determination is made whether ventricular fibrillation is occurring. If so, the microcontroller sends a signal to the defibrillator 16 to cause charging of its high-voltage storage capacitors and then will deliver either a shock command or a dump command to the defibrillator, depending upon whether the defibrillation episode is still persisting at the time that the defibrillator 16 returns a signal to the programmable microcontroller 12 indicative of the desired charge state of the defibrillator's storage capacitors.

The programmable microcontroller 12 also permits the bradycardia pacemaker to be operated in any one of several modes including an atrial tracking mode (either DDD or VDD).

With continued reference to FIG. 1, and in accordance with the present invention, the pacemaker portion of the combined system 10 may also operate in a rate-responsive mode and, in this regard, a physiologic sensor device, here shown as an activity sensor 54, provides an input to the programmable microcontroller 12, via I/O circuit 44. The activity sensor 54 may comprise an accelerometer of the type described in the Meyerson et al U.S. Pat. No. 5,179,947 which is assigned to applicant's assignee. As is well known in the art, rate responsive pacemakers are designed to adjust the cardiac stimulating rate to meet the patient's hemodynamic need as determined by an appropriate sensor so as to cause the pacing rate to operate at and between a lower programmed rate limit and an upper programmed rate limit.

Figure 3:
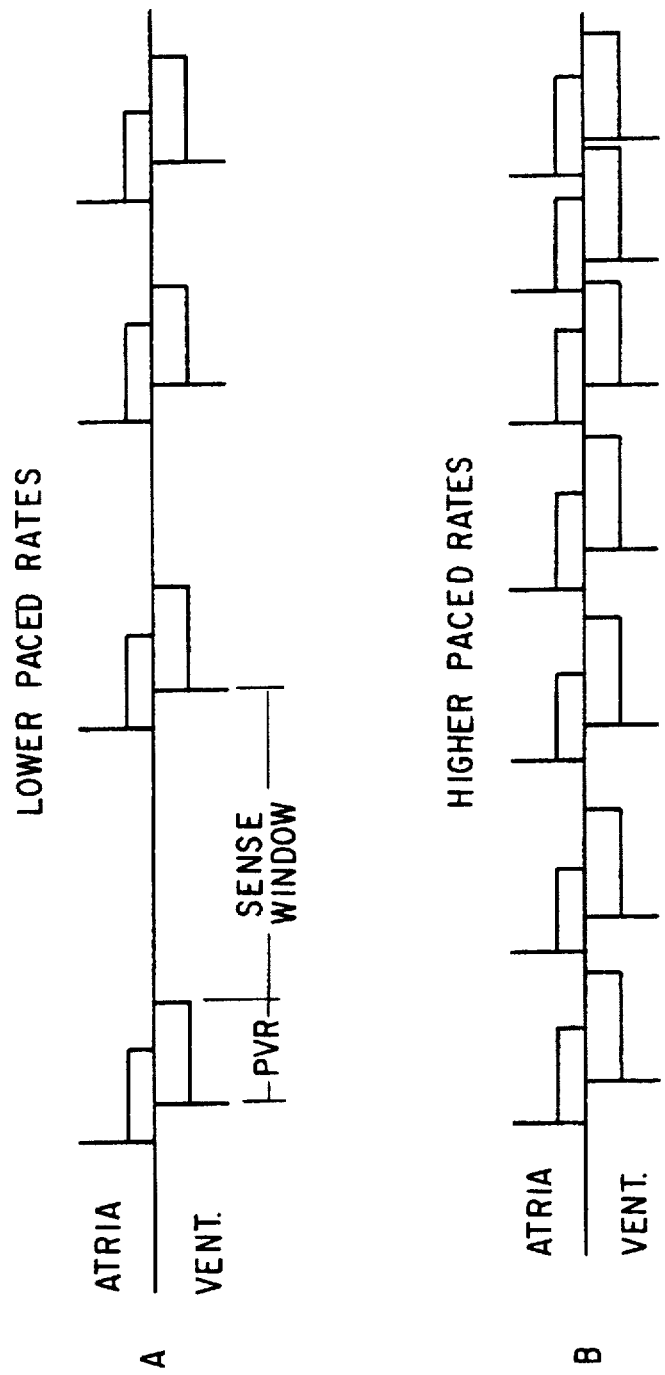
FIG. 3 is a waveform plot illustrating the impact on the devices' ventricular sensing window of a fixed refractory period with increasing pacing rates.

Irrespective of whether the rate increase is due to higher atrial rates when operating in the atrial tracking mode or due to higher sensor induced rates when operating in a rate sensitive mode, if the programmed paced ventricular refractory period (PVR) is a fixed quantity, as the paced ventricular rate increases, the ventricular sense window can decrease to the point where it becomes so short that ventricular depolarization events are inhibited throughout substantially the entire cardiac cycle and the defibrillator is therefore unable to react to ventricular depolarization events which may be indicative of tachycardia or ventricular fibrillation. FIG. 3 illustrates the shortening of the sense window with increasing pacing rate when a fixed refractory period is employed.

Figure 4:
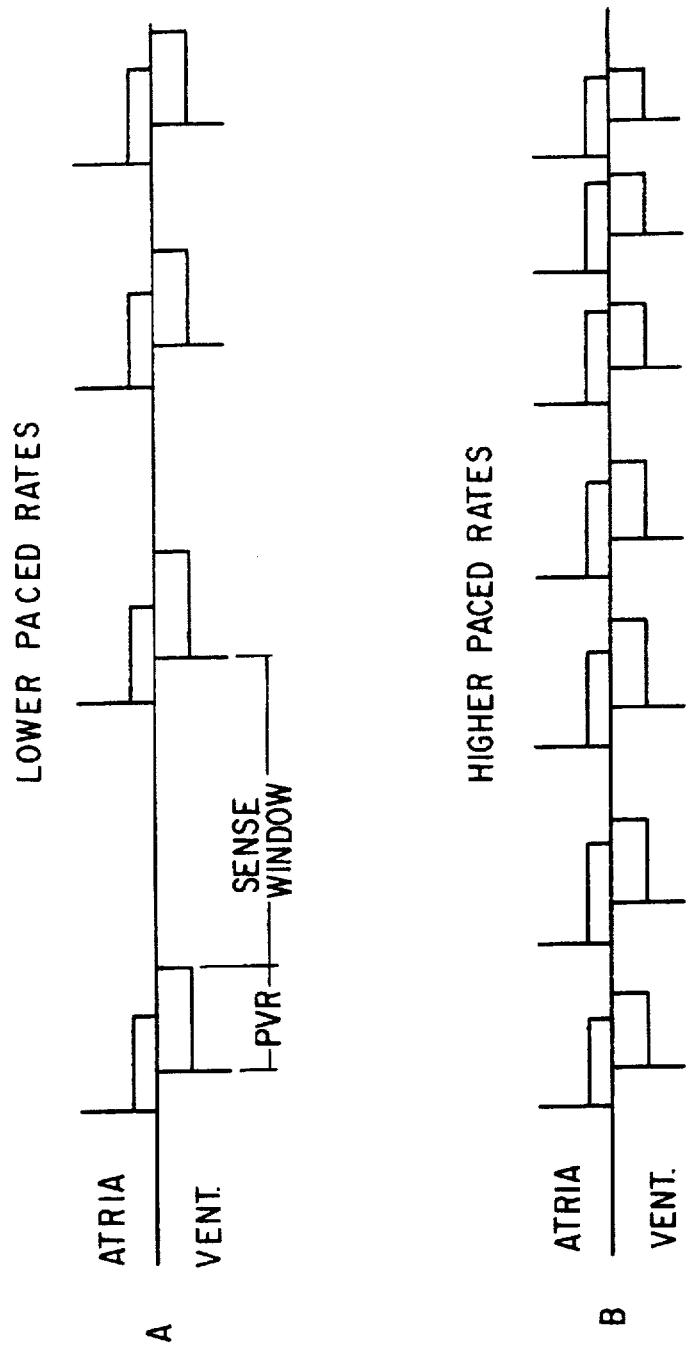
FIG. 4 is a waveform similar to that of FIG. 3, but with a dynamic refractory period.

In accordance with the present invention, however, a dynamic paced ventricular refractory period is provided for. As can be seen in the waveform plot of FIG. 4, rather than having a fixed, programmed value for PVR, the length of the PVR is made to vary inversely with the paced ventricular rate of the pacemaker. Thus, as the pacing interval becomes shorter, so, too, does the PVR value to thereby maintain an ample sense window even at rates approaching or equal to the physician programmed upper rate limit for the device.

In implementing the present invention, setup in the ROM memory 38 of the microprocessor is a table of values as illustrated in FIG. 5.

The table entries are addressed by computing an index in accordance with the following formulae:

URL INDEX=Int (1.024*60000)/Int (URL)/64)

LRL INDEX=Int (1.024*60000)/Int (LRL)/64)

where URL and LRL are in units of beats per minute. For the actual dynamic refractory (between the URL and LRL) indices used for a given range of and index, the length of that refractory is calculated as:

Dynamic Ref=(URL Ref.+round (y*z)

where y=(LRL Ref–URL Ref)/((60000/LRL)–(60000/URL))

z=(60000/((60000*1.024)/((the Index*64)+63)))–(60000/URL)

LRL and URL are in units of beats per minute LRL Ref and URL Ref are in units of milliseconds and the Index is a table index between URL Index and LRL Index.

The memory table is preloaded by the physician with values of the ventricular refractory interval and associated with each are a range of heart rate values which in the table of FIG. 5, are measured in units of beats per minute. The ventricular refractory period is a minimum when the pacing rate is at the URL, and a maximum when the pacing rate is at the LRL. Examining the table of FIG. 5 reveals that the URL had been set at about 120 beats per minute and the LRL at about 60 beats per minute. Thus, for index values between 8 and 16, the refractory interval is shown to increase from 150 milliseconds to 250 milliseconds. Each time the microprocessor computes the V—V interval, i.e., the pacing rate for the present beat, it executes the routine illustrated in FIG. 6, computing the appropriate index and thereby developing an address for the appropriate entry in the table for the ventricular refractory period associated with the computed rate.

Figure 6:
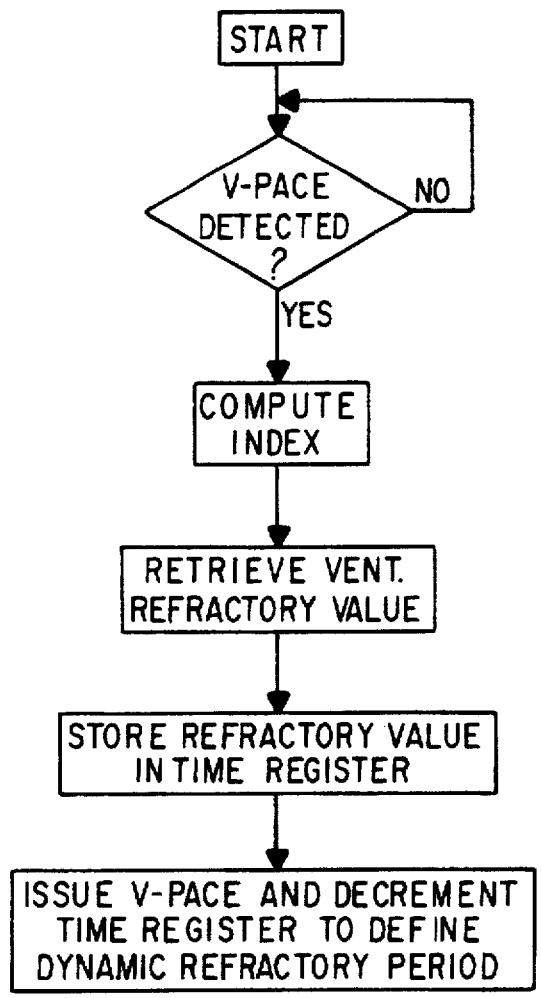
FIG. 6 is a flow diagram for the software algorithm executed by the microprocessor for establishing a paced ventricular refractory period that varies with measured ventricular stimulating rate.

Referring to the software flow chart of FIG. 6, upon the detection of a paced ventricular beat, the microprocessor 34 computes an index value using the above equation and the value so computed is used as a memory address to retrieve the appropriate ventricular refractory value from the table stored in memory 38. This value is then transferred to a hardware timing register in the microprocessor. The microprocessor then sends a control signal to the pacemaker pulse generator 14 and begins decrementing the contents of the hardware register at a fixed rate determined by the microprocessor's clock circuitry to thereby define a dynamic refractory period which ends when the value previously entered into the hardware register is counted down to zero.

This invention has been described herein in considerable detail in order to comply with the patent statutes and to provide those skilled in the art with the information needed to apply the novel principals and to construct and use such specialized components as are required. However, it is to be understood that the invention can be carried out by specifically different equipment and devices, and that various modifications, both as to equipment details and operating procedures, can be accomplished without departing from the scope of the invention itself.

What is claimed is:

1. A pacemaker and defibrillator combined in a common implantable housing, comprising:
    (a) first means for sensing atrial depolarization events and producing a first control signal in response thereto;
    (b) second means for sensing ventricular depolarization events and producing a second control signal in response thereto, the first and second means being shared by said pacemaker and defibrillator;
    (c) first pulse generator means for applying pacing pulses to a heart of a subject in whom said housing is implanted;
    (d) second pulse generator means for applying a defibrillating shock to said heart when said second control signals are produced at a rate exceeding a predetermined value;
    (e) microprocessor-based controller means operatively coupled to receive the first and second control signals for controlling the operation of the first and second pulse generator means wherein the first pulse generator means produces pacing pulses if a predetermined atrial ventricular delay interval elapses following receipt of the first control signal without receipt of the second control signal, the production of a pacing pulse by the first pulse generator means initiating a dynamic refractory period during which sensed ventricular depolarization events are ignored, the length of the refractory period being inversely proportional to a rate at which the pacing pulses are generated, whereby a sufficient interval is provided between adjacent refractory periods for allowing detection of ventricular depolarization events by the second sensing means at elevated rates of pacing pulse generation, the microcontroller being responsive to the ventricular depolarization events at the elevated rates of pacing pulse generation for enabling the defibrillator to deliver a cardioverting shock.

2. The pacemaker and defibrillator as in claim 1 wherein the length of the refractory period varies substantially linearly between a first preprogrammed value associated with a programmed lower pacing rate limit for the pacemaker, and a second preprogrammed value associated with a programmed upper pacing rate limit for the pacemaker.

3. The pacemaker and defibrillator as in claim 2 wherein the first preprogrammed value is about 300 milliseconds and the second preprogrammed value is about 150 milliseconds.

* * * * *